United States Patent [19]

Robinson

[11] 4,051,131
[45] Sept. 27, 1977

[54] INTERMEDIATES FOR PREPARING CEPHALOSPORINS

[75] Inventor: Charles A. Robinson, West Chester, Pa.

[73] Assignee: American Home Products Corporation (Del.), New York, N.Y.

[21] Appl. No.: 669,135

[22] Filed: Mar. 22, 1976

Related U.S. Application Data

[62] Division of Ser. No. 310,511, Nov. 29, 1972, Pat. No. 3,965,098.

[51] Int. Cl.$^2$ ........................................... C07D 501/18
[52] U.S. Cl. ..................................... 544/28; 424/246; 544/23; 544/30
[58] Field of Search ..................................... 260/243 C

[56] References Cited

U.S. PATENT DOCUMENTS

| | | | |
|---|---|---|---|
| 3,694,437 | 9/1972 | Jackson | 260/243 C |
| 3,741,959 | 6/1973 | Looker et al. | 260/243 C |

FOREIGN PATENT DOCUMENTS 806,868  11/1972  Belgium

Primary Examiner—Nicholas S. Rizzo
Attorney, Agent, or Firm—Stephen Venetianer

[57] ABSTRACT $\Delta^3$-Cephalosporins are prepared by reacting novel diorganodihalosilane or monorganodihalosilane derivatives of 7-aminocephalosporanic acid ("7ACA") and 7-amino-desacetoxycephalosporanic acid ("7ADCA") with known acylating agents followed by hydrolysis or alcoholysis to produce $\Delta^3$-cephalosporins with useful antibiotic activity. The dialkyldihalosilane derivatives are prepared by adding a base such as triethylamine slowly to a mixture of 7ACA or 7ADCA and a dialkyldihalosilane.

7 Claims, No Drawings

INTERMEDIATES FOR PREPARING CEPHALOSPORINS

This is a division, of application Ser. No. 310,511, filed Nov. 29. 1972 and now issued as U.S. Pat. No. 3,965,098.

BACKGROUND OF THE INVENTION

1. Field of the Invention

This invention relates to novel organosilane derivatives of 7-aminocephalosporanic acid ("7ACA") and 7-amino-desacetoxycephalosporanic acid ("7ADCA"). More specifically, this invention relates to the use of these novel organosilane derivatives for the synthesis of $\Delta^3$-cephalosporins. Additionally, this invention deals with a specified set of reaction conditions whereby $\Delta^3$-cephalosporins are produced utilizing the above organosilane derivatives without the formation of the less desirable $\Delta^2$-isomers.

2. Description of the Prior Art

The use of tri-organo substituted silane ("silyl") intermediates for the synthesis of cephalosporins from 7-ACA and 7-ADCA has been described in several patents and is well known in the prior art. However, the use of di-organo substituted silane ("silene") intermediates for the synthesis of cephalosporins has been described only fleetingly in the prior art.

For example, British Pat. No. 1,073,530 discloses the synthesis of cephalosporins by silylating "7ACA" with monohalosilanes, silazanes or silylamines followed by acylating the intermediate trialkyl silyl derivative of "7ACA". U.S. Pat. No. 3,671,449 discloses mono and di-silylated "7ACA" and "7ADCA" and processes for their preparation with mono or bissilylamides, silylureas and silylurethanes as silylating agents. Additionally, this particular patent discusses various reasons why halosilanes should not be used as silylating agents.

Netherlands Pat. No. 6,401,841 deals with the use of dialkyldihalosilanes in preparing 6-aminopenicillanic acid intermediates. This patent also mentions the possibility that aminocephalosporanic acid can be used in this procedure.

Netherlands Pat. No. 7,105,259 discloses and claims the preparation of cephalosporins by reacting 7ACA and 7ADCA with a dialkoxydihalosilane or an alkylene dioxydihalosilane, acylating the intermediate and hydrolyzing the resulting product. This patent is the only patent in the cephalosporin prior art which actually exemplifies silylation or silenation with a halosilane. However, there is no mention in the above prior art of the problem of isomerization of the double bond of $\Delta^3$-cephalosporins and particularly esters of $\Delta^3$-cephalosporins to the less active $\Delta^2$-isomers by the action of bases such as triethylamine or pyridine. This problem is discussed in an article by J. D. Cocker, et. al. entitled Cephalosporanic Acids. Part IV 7-Acylamidoceph-2-em-4-carboxylic Acids appearing in the Journal of the Chemical Society 1966, 1142.

SUMMARY OF THE INVENTION

The present invention provides a method for synthesizing $\Delta^3$-cephalosporins. The method utilizes new di-organo or mono organo substituted silane derivatives of 7-ACA and 7ADCA which hereinafter will be referred to as "silenated" derivatives. The silenated derivatives can be represented by the following formula:

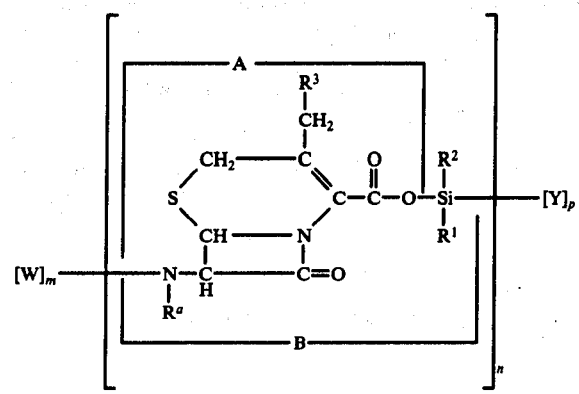

wherein:

$R^1$ is of the group consisting of hydrogen, alkyl, aryl and aralkyl $R^2$ is of the group consisting of alkyl, aryl and aralkyl $R^3$ is hydrogen or

$R^a$ is of the group consisting of hydrogen, and the alkanoyl, aryloxyalkanoyl, heterocyclicalkanoyl, aroyl and aralkanoyl residues of organic carboxylic acids;

W is of the group consisting of hydrogen and

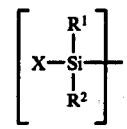

wherein $R^1$ and $R^2$ have the same meaning as before, and X is halogen;

m and p are integers from 0 to 1 and are always equal n is an integer from 1 to about 25;

Y is of the group consisting of halogen, and groups of the following formula:

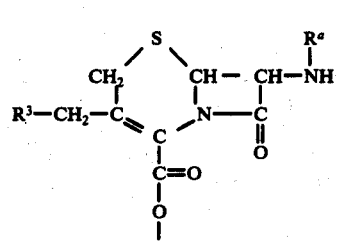

wherein $R^a$ has the same meaning as before; with the provisos that, in Formula I, 1. when m is 0 and p is 0, n is more than 1;

2. when n is more than 1, the moieties A of the additional groups B recur in random head-toward-head, head-toward-tail and tail-toward-tail disposition;

3. when W is hydrogen, n is 1, and Y is Formula III, then $R^a$ is hydrogen.

DESCRIPTION OF SPECIFIC EMBODIMENTS

In this specification, the nomenclature refers to the numbering of the "cephem" structure [see J. Am. Chem. Soc. 84, 3400 (1962)] with Δ³ indicating a double bond in the 3,4-position and Δ² indicating a double bond in the 2,3-position.

The new silenated 7-ACA or 7-ADCA derivatives of formula I, wherein R$^a$ is hydrogen, are prepared by reaction of 7-ACA or 7ADCA or a salt thereof, preferably in the presence of an acid acceptor, and also preferably in an inert organic solvent, with a di-halosilane of the following formula:

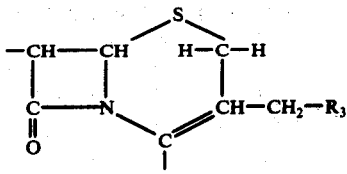

V.

are considered to be involved:

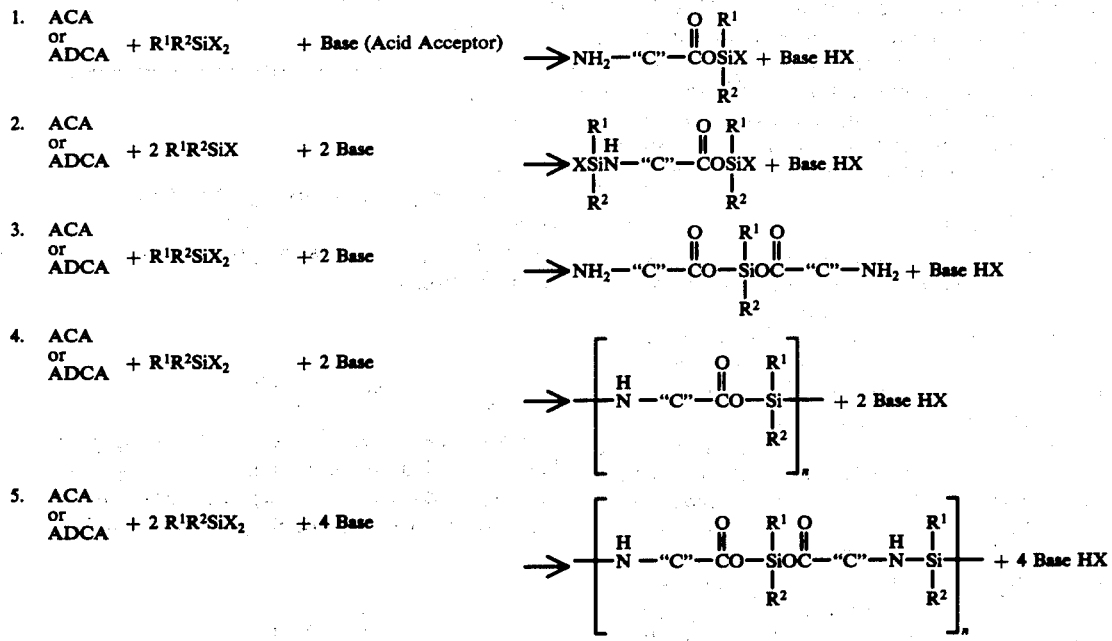

IV.

$$X-\underset{\underset{R^2}{|}}{\overset{\overset{R^1}{|}}{Si}}-X$$

wherein R¹, R² and X have the same meanings as in formula I above, and the reaction is continued until formation of the salt of the respective hydrogen halide is substantially complete or until substantially all of the 7-ACA or 7-ADCA is reacted. Suitable di-halosilanes include for example dimethyldichlorosilane, methylpropyldichlorosilane, dimethyldibromosilane, dibutyldichlorosilane, diphenyldichlorosilane, methylphenyldichlorosilane, dibenzyldichlorosilane and ethylbenzyldibromosilane and monomethyldichlorosilane.

In the silenation of 7ACA or 7ADCA according to the present invention, various proportions of di-halosilanes and acid acceptors can be employed to give various novel silenated products which contain a half to two silicon groups per ACA or ADCA group, and in which one or two of the halogen atoms of the di-halosilane have reacted. For example, the following reactions wherein C= 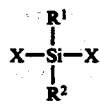

The products containing more than one "C" unit (i.e., wherein n > 1 in the foregoing formulae) are considered to be linear or cyclic dimers, trimers and the like, or polymers. In such cases, the repeating ACA or ADCA moieties of the group units may be randomly disposed head-toward-tail, head-toward-head and/or tail-toward-tail in a given compound, as will be understood by those skilled in the art and referred to hereinbefore.

The products of the invention can be prepared successfully using one-half to two moles of halosilane per mole of ACA or ADCA. Suitable acid acceptors for the silenation reaction include ammonia, organic amines, alkali metal carbonates, alkaline earth metal carbonates and the like. In general, it is preferred to use anhydrous ammonia or an amine, such as triethylamine or diethylamine. Greatest efficiency is obtained by using no more than two equivilents of base per mole of dihalosilane.

For use as solvent media in the silenation of ACA or ADCA to obtain the products of the invention, a wide range of anhydrous non-hydroxylic organic solvents are suitable, including chlorinated solvents such as methylene chloride, chloroform and ethylene dichloride; ethers such as tetrahydrofuran; and other solvents such as methylisobutylketone, dimethylformamide, ethyl acetate and acetonitrile.

Among these solvents, methylene chloride, chloroform, acetonitrile, and ethyl acetate are particularly useful. Since the halosilanes and the silenated products are decomposed by moisture and other hydroxylic agents, solvents employed as reaction media must be substantially anhydrous and free from alcoholic impurities.

For the production of Cephalosporins of high purity, free from Δ²-isomerization by-products, the base employed as acid acceptor is added slowly to a mixture of the dihalosilane and ACA or ADCA in a suitable solvent medium at a temperature at which silenation proceeds readily, e.g. 0°-20° C. The silenation reaction may be completed at a higher temperature, e.g. up to the boiling point of the solvent, if required. In refluxing methylene chloride, for example, the reaction of one mole of ACA with one mole of dimethyldichlorosilane and two moles of triethylamine is complete in one hour. Complete solubility of the ACA or ADCA used as a starting material and a quantitative yield of base hydrohalide are generally indicative of complete reaction. During these operations, it is essential that the total quantity of base used be limited to two equivalents per mole of dihalosilane in order to avoid an excess at any point in the reaction. Less than this amount can be employed without danger of an excess at the end of the addition.

The silenated 7-ACA or 7-ADCA derivatives prepared according to this invention can be isolated by removing the base hydrohalide by filtration and distillation of the solvent, or if these intermediates are to be converted at once to a cephalosporin, the reaction mixture can be acylated directly without filtration or concentration. The new silenated derivatives of ACA or ADCA are readily soluble in a wide selection of anhydrous, non-hydroxylic solvents such as methylene chloride, chloroform, ethyl acetate, tetrahydrofuran, dimethylsulfoxide, dimethylacetamide, dimethylformamide, acetonitrile, and methylisobutylketone. The β-lactam ring of the silenated derivatives is shown to be intact by infrared analysis as well as by the recovery of high purity 7-ACA or 7-ADCA on treatment with water or an alcohol.

The new acylated organosilane derivatives of 7ACA or 7-ADCA of formula I wherein $R^a$ is an acyl group, are prepared by reaction of the silenated 7-ACA or 7-ADCA intermediates with a suitable reactive derivative of an organic carboxylic acid. As will be known to those skilled in the art, the reactive derivative may be that of a suitable organic sulfonic acid instead of an organic carboxylic acid. The ultimate cephalosporins are obtained by hydrolysis or alcoholysis of these acylated derivatives to the cephalosporin per se. Suitable acylating agents include carboxylic acid halides, carboxylic acid anhydrides, mixed anhydrides with other carboxylic or inorganic acids. For the preparation of aminocephalosporins, amino acid chloride hydrochlorides and amino acid N-carboxyanhydrides are suitable for acylating the ACA or ADCA derivatives.

Although not limited thereto, silenated cephalosporin derivatives of particular interest are those of formula I wherein $R^a$ is selected from the group consisting of 2-thienylacetyl, phenylglycyl, dihydrophenylgylcyl, 4-pyridylthioacetyl, cyanoacetyl, 1-tetrazolylacetyl, 2-furylacetyl, phenylgylcolyl, phenylacetyl, phenoxyacetyl, 1-aminocyclohexylcarbonyl, and Sydnonylacetyl.

Illustrative of some of the preferred acylating agents are the reactive derivatives of $R_a$ such as halides.

The acylation reaction is carried out preferably in the presence of an acid acceptor which may be the same or different from the one employed in preparing the silenated intermediate. However, the use of a weak base such as N,N-dimethylaniline or quinoline, in the acylation reaction avoids isomerization to Δ²-cephalosporin by-products and is preferred for use in the preparation of α-amino cephalosporins by acylation with α-amino halide hydrohalides.

In general, the same types of solvents are useful for the acylation of the silenated 7-ACA or 7-ADCA products as for their original preparation. The silenated cephalosporins of the present invention are readily hydrolyzed or alcoholyzed by treating with water or other hydroxyl-containing compound, e.g., an alcohol such as methyl or ethyl alcohol, to form the corresponding cephalosporins.

A particular advantage of this invention lies in the synthesis of Δ³-cephalosporins without forming the undesirable Δ² isomers. It has been found that when a base such as triethyl amine, is added slowly to a suspension of 7ACA or 7ADCA and a di-organo substituted halosilane, followed by acylation and hydrolysis, the product contains minimal amounts of the Δ²-isomer. This is in direct contrast to the products obtained when the di-halosilane is added to a mixture of 7ACA or 7ADCA and base as is done in the penicillin art.

For example, silenation of ACA by the procedure of this invention followed by hydrolysis afforded an 84% recovery of ACA containing 1% of the Δ² isomer, while conventional silenation procedures resulted in a product containing 42% of the Δ²-isomer as shown by optical rotation. The specific rotations of 7ACA and iso-7ACA have been reported as +114° and +551 inches, respectively [B. Fechtig et al, Helv. Chim Acta 51(5), 1116 (1968)]. Similarly, the silenation of ADCA by the preferred procedure followed by hydrolysis provided a 90% recovery of ADCA containing approximately 1% of the Δ²-isomer, compared to a content of about 15% by conventional silenation procedures. Authentic 7ADCA, free of isomer by thin layer chromatography, has a specific rotation $[\alpha]_D^{20}$ +211°(1% in 0.5 N NaHCO$_3$).

AS further illustrated in the examples below, the production of Sodium Cephalothin by silenation of ACA following the procedure of this invention followed by acylation and hydrolysis gave an 81% yield of the Cephalosporin containing less than 2% of the Δ²-isomer compared to 23% when conventional silenation procedures were followed. These values calculated from specific rotations are in good agreement with NMR analysis which indicated 0 and 23% isomerization, respectively. Sodium Cephalothin and its Δ²-isomer have been reported by J. D. Cocker et al (J. Chem. Soc. 1966 1142) to exhibit $[\alpha]_D$ of +133° and 438°.

EXAMPLE I

Silenation of 7-Aminocephalosporanic Acid

In a 125 ml. 3-neck flask fitted with stirrer, thermometer, nitrogen inlet, and drying tube, a suspension of 2.72 g. (0.010 mole) of 7ACA in 25 ml. of dry methylene chloride was cooled to 16° C. under dry nitrogen and 1.29 g (0.010 mole) of dimethyldichlorosilane in 5 ml. of methylene chloride was added rapidly. Then, a solution of 2.02 g. (0.020 mole) of triethylamine in 12 ml. of methylene chloride was added dropwise from a dropping funnel at 20°-21° C over 15 minutes with rapid stirring. The reaction was completed by heating the mixture at 38°40° C. for one hour.

After cooling to 10° C. under nitrogen, the pale tan mixture was poured into 20 ml. of ice-water with stirring, 7ACA crystallized rapidly; pH of mixture, 3.7. The mixture was allowed to stir for one-half hour, and the 7ACA was collected by filtration, washed by stirring in 50% aqueous acetone, and finally washed on the filter with acetone. The recovery, after drying, was 2.28 g. or 84%; $[\alpha]_D^{20}$ +118.5° (1% in 0.5 N $NaHCO_3$); β-lactam (iodometric) assay, 95%.

EXAMPLE 2

When the silenation was carried out in a manner conventional for penicillins by adding dropwise a solution of 1.29 g. of dimethyldichlorosilane in methylene chloride to a mixture of 2.72 g. of 7ACA and 2.02 g. of triethylamine in methylene chloride at 20° C. over one-half hour and immediately quenching the mixture in 20 ml. of ice-water, the recovery was 1.60 g. or 59%; $[\alpha]_D^{20}$ +299.6° (1% in 0.5 N $NaHCO_3$).

EXAMPLE 3

The procedure of Example I was repeated except that 1.46 g (0.020 mole) of diethylamine was used in place of triethylamine and the reaction was completed by stirring at 20° C. for one hour. The recovery of 7ACA was 2.38 g. or 88% $[\alpha]_D^{20}$ +108.4°; β-lactam (iodometric) assay 97%.

EXAMPLE 4

The procedure of Example I was repeated except that 48 ml. of a 0.41 N solution of anhydrous ammonia in methylene chloride was used in place of the triethylamine solution and the reaction was continued at 21° C. for one hour. The recovery of 7ACA was 2.34 g. or 86%; $[\alpha]_D^{20}$ +105.6°; β-lactam (iodometric) assay, 97%.

EXAMPLE 5

The procedure of Example I was repeated except that acetonitrile was used in place of methylene chloride as reaction medium and the reaction was completed by stirring at 38°-40° C. for 45 minutes. The recovery of 7ACA was 2.32 g. or 85% $[\alpha]_D^{20}$ +108.2°; β-lactam (iodometric) assay, 96%.

EXAMPLE 6

Silenation of 7-Aminodesacetoxycephalosporanic Acid

In a 125 ml. 3-neck flask fitted with stirrer, thermometer, nitrogen inlet, and drying tube, a suspension of 2.14 g. (0.010 mole) of 7ADCA in 25 ml. of methylene chloride was treated with 1.29 g. (0.010 mole) of dimethyldichlorosilane in 5 ml. of methylene chloride and the mixture was cooled to 15° C. Then, a solution of 2.02 g. (0.020 mole) of dry triethylamine in 12 ml. of methylene chloride was added dropwise from a dropping funnel at 15°-18° C. over one-half hour with rapid stirring. The reaction was completed by heating the mixture at 38°-40° C. for 20 minutes.

After cooling to 10° C. under nitrogen, the yellow mixture was poured into 20 ml. of ice-water with stirring. 7ADCA crystallized rapidly; pH, 3.8. After stirring for one-half hour, the 7ADCA was collected by filtration, washed with aqueous acetone and finally with acetone. The recovery, after drying, was 1.93 g. or 90%; $[\alpha]_D^{20}$ +217.7° (1% in 0.5 N $NaHCO_3$); iodometric assay 102%; one spot by thin layer chromatography.

EXAMPLE 7

When the silenation was carried out in a manner conventional for penicillins by adding a solution of 1.29 g. of dimethyldichlorosilane in methylene chloride to a suspension of 2.14 g. of 7ADCA and 2.02 g. of triethylamine in methylene chloride at 15°-18° C. over one-half hour and allowing the mixture to react at 38°-40° C. for 20 minutes before quenching in water, the recovery was 1.92 g. or 90%; $[\alpha]_D^{20}$ +292.7° (1% in 0.5 N $NaHCO_3$); thin layer chromatography showed the presence of the $\Delta^2$-isomer of 7-ADCA

EXAMPLE 8

Sodium salt of 7-(2-thienylacetamido)-cephalosporanic Acid

In a 125 ml. 3-neck flask fitted with stirrer, thermometer, nitrogen inlet and drying tube, a suspension of 2.72 g. (0.010 mole) of 7-aminocephalosporanic acid in 25 ml. of methylene chloride was cooled to 5° C. under dry nitrogen and 1.29 g. (0.010 mole) of dimethyldichlorosilane in 5 ml. of methylene chloride was added. Then, a solution of 2.02 g. (0.020 mole) of triethylamine in 12 ml. of methylene chloride was added dropwise from a dropping funnel at 3°-5° C. over 13 minutes with rapid agitation.

After stirring for an additional 15 minutes at 5° C., the cloudy solution was treated with 1.21 g. (0.010 mole) of N,N-dimethylaniline in 3 ml. of methylene chloride followed by the dropwise addition at 0°-3° C. of 1.69 g. (0.105 mole) of 2-thienylacetyl chloride in 4 ml. of methylene chloride. After allowing the mixture to warm to 20° C., stirring was continued for two hours.

The pale tan solution was cooled to 5° C. and poured into 60 ml. of ice-water with stirring. After adjusting the pH to 1.1 with hydrochloric acid, the layers were separated and the aqueous portion re-extracted with methylene chloride. Ice-water (40 ml.) was added to the combined methylene chloride extracts and the mixture was neutralized to pH 7 with dilute sodium hydroxide solution. After separating the layers and re-extracting the methylene chloride phase with water, the combined aqueous extracts were washed with methylene chlorine to remove dimethylaniline.

A mixture of the aqueous phase and 30 ml. of ethyl acetate was adjusted to pH 1.8 with dilute hydrochloric acid at 10° C. The water layer was separated and re-extracted with ethyl acetate. The combined ethyl acetate extracts, after drying over anhydrous sodium sulfate, were treated with 12.5 ml. of a 0.77 N solution of sodium 2-ethylhexanoate in dry n-butanol. The white crystalline product was collected by filtration, washed with ethyl acetate and dried under vacuum; yield, 3.39 g. or 81% of theory; purity by bioassay, 90.5%; $[\alpha]_D^{20}$ +139.1° (1% in water) NMR ($D_2O$), no peak at 3.6 $\approx\tau$ for the vinyl 2-proton characteristic of $\Delta^2$ unsaturation.

EXAMPLE 9

When the silenation was carried out in a manner conventional for penicillins by adding dropwise a solution of 1.29 g. of 7ACA and 2.02 g. of triethylamine in methylene chloride at 5°-7° C. over eight minutes and allowing the mixture to stir at 20° C. for 2 hours, the procedure was continued as described in Example 8 to give a yield of 3.26 g. or 78% of theory; $[\alpha]_D^{20}$ +201.8°; NMR ($D_2O$), broad singlet at 3.6 $\approx\tau$ corresponding to 23% $\Delta^2$ unsaturation by integration.

EXAMPLE 10

7-(D-α-aminophenylacetamido)cephalosporanic acid ("Cephaloglycin")

In a 125 ml. 3-neck flask fitted with stirrer, thermometer, nitrogen inlet, and drying tube, 1.30 g. of dimethyldichlorosilane was added to 2.72 g. of 7ACA in 30 ml. of methylene chloride. Then, a solution of 2.02 g. of triethylamine in 12 ml. of methylene chloride was added dropwise at 19°–21° C. over 17 minutes with stirring. After heating the mixture under reflux condenser at 38°–40° C. for one-half hour, it was cooled under nitrogen.

The yellow solution containing crystals of triethylamine hydrochloride was treated with 1.21 g. of N,N-dimethylaniline followed by the portionwise addition of 2.06 g. of D-phenylglycyl chloride hydrochloride with ice-bath cooling. After allowing the mixtures to warm to 18° C., stirring was continued for 45 minutes.

The turbid solution was cooled and poured into 30 ml. of ice and water with stirring and then clarified by filtration through Celite. On adjusting the pH of the filtrate to 4.2 with 5 N sodium hydroxide solution, crystallization proceeded rapidly. The white product was collected by filtration, washed, and dried under vacuum; yield, 1.95 g.; moisture, 7.0%; bioassay, 91% (anhydrous basis).

EXAMPLE 11

7-(D-α-aminophenylacetamido)-desacetoxycephalosporanic acid ("Cephalexin")

In a 125 ml. 3-neck flask fitted with stirrer, thermometer, nitrogen inlet and drying tube, 1.29 g. of dimethyldichlorosilane was added to 2.14 g. of 7ADCA in 30 ml. of methylene chloride. Then, a solution of 2.02 g. of triethylamine in 12 ml. of methylene chloride was added dropwise at 20°–22° C. over 16 minutes with stirring. After heating the mixture under reflux condenser at 38°–40° C. for 45 minutes, it was cooled under nitrogen.

The cloudy, amber solution was treated with 1.21 g. of N,N-dimethylaniline followed by the portionwise addition of 2.06 g. of D-phenylgylcyl chloride hydrochloride at 0° to 3° C. After allowing the mixture to warm to 18° C., stirring was continued for 1½ hours.

The mixture was cooled and poured into 40 ml. of ice-water with stirring; pH 1.3. After separating the layers, the pale yellow aqueous layer was clarified by filtration, concentrated under vacuum to a volume of 17 ml., and finally diluted with 18 ml. of methanol. On adjusting the pH to 4.1 at 40° C., crystallization proceeded rapidly. The white product was collected by filtration, washed with ice-water, and dried under vacuum; yield, 2.50 g.; moisture, 5.2%. Recrystallization of this material afforded Cephalexin of 92% purity by bioassay.

I claim:

1. A compound of the group consisting of those having the following formula:

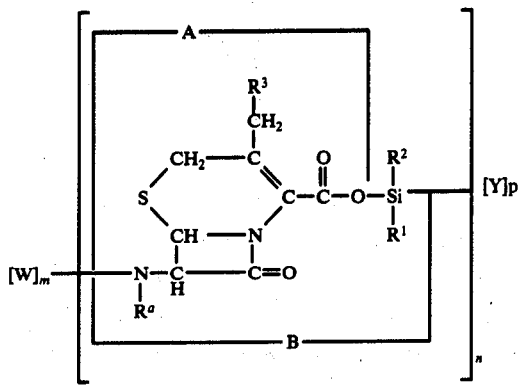

wherein:
$R^1$ is of the group consisting of hydrogen, lower alkyl, phenyl, loweralkylphenyl and benzyl
$R^2$ is of the group consisting of lower alkyl, phenyl, loweralkylphenyl and benzyl
$R^3$ is hydrogen or

$R^a$ is of the group consisting of tetrazolylacetyl and sydnonylacetyl; W is of the group consisting of hydrogen and

II

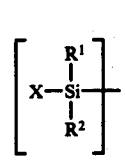

wherein $R^1$ and $R^2$ have the same meaning as before, and X is halogen;
$m$ and $p$ are integers from 0 to 1 and are always equal
$n$ is an integer from 1 to about 25;
Y is of the group consisting of halogen, and groups of the following formula:

III

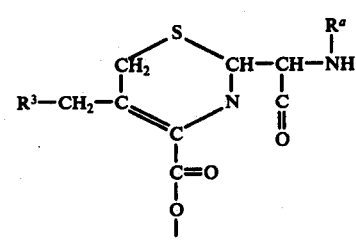

wherein $R^a$ has the same meaning as before; with the provisos that, in Formula I,
1. when $m$ is $o$ and $p$ is 0, $n$ is more than 1;
2. when $n$ is more than 1, the moieties A of the additional groups B recur in random head-toward-head, head-toward-tail and tail-toward-tail disposition;
3. when W is hydrogen, $n$ is 1, and Y in Formula III, then $R^a$ is hydrogen,
4. when W is hydrogen or

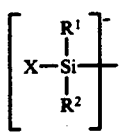

2. A compound as defined in claim 1, wherein $m$ and $p$ are both 0 and $n$ is greater than 1.

3. A compound as defined in claim 1, wherein W is hydrogen; $m$ is 1; $p$ is 1; and Y is Formula III.

4. A compound as defined in claim 1, wherein W is

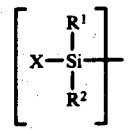

$m$ is 1; $p$ is 1; and Y is halogen.

5. A compound as defined in claim 1, wherein W is hydrogen; $m$ and $p$ are 1; and Y is halogen.

6. A compound as defined in claim 1, wherein $R^1$ and $R^2$ are alkyl.

7. A compound as defined in claim 6, wherein $R^1$ and $R^2$ are methyl.

* * * * *

UNITED STATES PATENT OFFICE
CERTIFICATE OF CORRECTION

PATENT NO. : 4,051,131
DATED : September 27, 1977
INVENTOR(S) : Charles A. Robinson It is certified that error appears in the above-identified patent and that said Letters Patent are hereby corrected as shown below:

Claim 1, column 10, line 52, Formula III should read

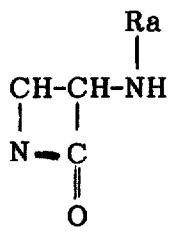

Claim 1, column 11, line 5,

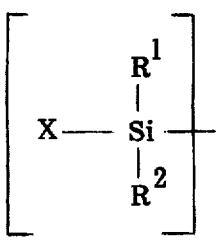   "Y is not halogen when n is one"

Signed and Sealed this

Twenty-seventh Day of March 1979

[SEAL]

Attest:

RUTH C. MASON
Attesting Officer

DONALD W. BANNER
Commissioner of Patents and Trademarks